United States Patent [19]

Liepa

[11] Patent Number: 5,565,581
[45] Date of Patent: Oct. 15, 1996

[54] EPOXIDATION OF OLEFINS

[75] Inventor: Mark A. Liepa, West Chester, Pa.

[73] Assignee: ARCO Chemical Technology, L.P., Greenville, Del.

[21] Appl. No.: 599,763

[22] Filed: Oct. 18, 1990

[51] Int. Cl.$^6$ .................................................. C07D 313/00
[52] U.S. Cl. ........................... 549/346; 549/356; 549/509; 549/510; 549/529
[58] Field of Search ....................... 549/529, 346, 549/356, 509, 510

[56] References Cited

U.S. PATENT DOCUMENTS 3,862,961  1/1975  Sheng et al. .............................. 549/529
3,870,729  3/1975  Bost et al. ................................ 549/529
3,983,143  9/1976  Sheng et al. ............................. 549/529

FOREIGN PATENT DOCUMENTS 0188912   7/1986   European Pat. Off. .
0343959  11/1989   European Pat. Off. .

*Primary Examiner*—Amelia Owens
*Attorney, Agent, or Firm*—William C. Long

[57]         ABSTRACT

The present invention relates to the epoxidation of olefins using cyclohexyl hydroperoxide as reactant, the improvement being using a secondary or tertiary alcohol such as cyclohexanol or tertiary butyl alcohol as a stabilizing agent during the epoxidation, the alcohol stabilizer being fed to the epoxidation reaction zone in an amount greater than 3 moles per mole of hydroperoxide fed to the epoxidation reaction zone.

6 Claims, No Drawings

EPOXIDATION OF OLEFINS

BACKGROUND OF THE INVENTION

1. Field of the Invention

The present invention relates to the epoxidation of olefins by catalytic reaction with cyclohexyl hydroperoxide, the particular improvement being the provision of more than 3 moles of alcohol stabilizer per mole of hydroperoxide in the feed to the epoxidation reaction zone.

2. Description of the Prior Art

The catalytic epoxidation of olefinic materials by reaction with organic hydroperoxides is by now a well known reaction. Specifically, this epoxidation reaction employing cyclohexyl hydroperoxide as a reagent is described, for example, in U.S. Pat. Nos. 3,983,143 and 3,870,729 as well as in European Patent 0 129 814.

A patent which is especially relevant to the subject of this invention is U.S. Pat. No. 3,862,961. This patent describes the epoxidation of olefins by catalytic reaction of the olefin with cyclohexyl hydroperoxide in the presence of an alcohol stabilizing agent such as tertiary butyl alcohol. The patent teaches that there is a critical ratio of the stabilizing agent to the hydroperoxide, namely that the mole ratio of stabilizer to hydroperoxide must be in the range from 1:1 to 3:1, and preferably from 1.5:1 to 2.5:1,, See column 4, lines 21 through 24 of U.S. Pat. No. 3,862,961.

BRIEF DESCRIPTION OF THE INVENTION

It has now been found that advantageous results are achieved in the epoxidation of olefins such as propylene by reaction with cyclohexyl hydroperoxide where a $C_3$ to $C_9$ secondary or tertiary alcohol is employed as stabilizer in amounts above the specified critical upper mole ratio limit of 3:1 taught in U.S. Pat. No. 3,862,961. In accordance with the present invention, superior results are achieved in the catalytic epoxidation reaction where amounts of alcohol stabilizer in excess of a 3:1 mole ratio of alcohol to hydroperoxide are employed.

DETAILED DESCRIPTION

The present invention is applicable to the epoxidation of olefinic compounds generally, although the alpha olefins having about 2 to 20 carbon atoms are most advantageously reacted in accordance with the invention. The invention is especially applicable to the conversion of propylene to propylene oxide.

The hydroperoxide which is employed in practice of the invention is cyclohexyl hydroperoxide, a less stable hydroperoxide than tertiary butyl hydroperoxide and ethylbenzene hydroperoxide which are normally used in commercial practice of this reaction. Cyclohexyl hydroperoxide is conveniently prepared by the molecular oxygen oxidation of cyclohexane in the liquid phase. A preferred procedure for preparing cyclohexyl hydroperoxide as well as representative prior art teachings concerning this reaction can be found in co-pending application Ser. No. 07/590,620 filed Sep. 28, 1990 now U.S. Pat. No. 5,043,481.

Conventional epoxidation catalysts are employed. Particularly preferred is the use of soluble compounds of molybdenum, although other catalysts such as are described in U.S. Pat. No. 3,351,635, for example, can also be employed.

Essential to practice of the present invention is the provision of $C_3$ to $C_9$ secondary or tertiary alcohol as a stabilizing agent in the epoxidation reaction mixture.

As described in U.S. Pat. No. 3,862,961, the alcohol stabilizing agents which are employed in the method of the instant invention are the monohydric secondary and tertiary alcohols having from 3 to 9 carbon atoms in the molecule. Primary alcohols cannot be employed in the method of this invention since these attack the epoxide product thereby decreasing the yield of the epoxide because of side reactions and thus defeating the objects of this invention. Secondary and tertiary alcohols, however, are very much less reactive, with the tertiary being the least reactive with the epoxide.

Examples of secondary alcohols which can be employed are isopropyl alcohol (2-propanol); 2-butanol; 2-pentanol; 3-pentanol; 4-methyl-2-pentanol; 2-methyl-3-pentanol; 2,4-dimethyl-3-pentanol; 2-hexanol; 5-methyl-2-hexanol; 3-hexanol; 5-methyl-3-hexanol; 2-heptanol; 3-heptanol; 4-heptanol; 2,6-dimethyl-4-heptanol; 2-octanol; 3-octanol; 4-octanol; 2-nonanol; 3-nonanol; 4-nonanol; 5-nonanol; cyclohexanol; 2-methylcyclohexanol and the like.

Examples of the tertiary alcohols which can be employed are tertiary butyl alcohol (2-methyl-2-propanol); 2-methyl-2-pentanol; 2,4-dimethyl-2-pentanol; 3-methyl-3-pentanol; 2,3-dimethyl-3-pentanol; 3-ethyl-3-pentanol; 3-ethyl-2-methyl-3-pentanol; 2-methyl-2-hexanol; 3-methyl-3-hexanol; 3-ethyl-3-hexanol; 3-ethyl-5-methyl-3-hexanol; 2-methyl-2-heptanol; 3-methyl-3-heptanol; 4-methyl-4-heptanol; 4-ethyl-4-heptanol; 2-methyl-2-octanol; 2-phenyl-2-propanol and the like.

Preferred alcohol stabilizers are tertiary butyl alcohol and cyclohexanol.

The stabilizing alcohol is fed to the epoxidation zone in an amount relative to the hydroperoxide of greater than 3 moles alcohol per mole of hydroperoxide fed to the epoxidation zone. A preferred range of the mole ratio of alcohol stabilizer to hydroperoxide is 3.2:1 to 8:1, more preferably 3.5:1 to 5:1. It has been found, in contrast to the teaching of U.S. Pat. No. 3,862,961, that improved epoxidation results are achieved using these relative amounts of alcohol stabilizer and hydroperoxide.

In order to illustrate the present invention, the following examples are provided.

EXAMPLE

A series of batch epoxidation experiments were carried out employing propylene as the olefin and using cyclohexyl hydroperoxide which was contained in a cyclohexane oxidate as the epoxidation reagent. Varying amounts of different additive stabilizers were employed.

The conditions of the batch epoxidations involved temperatures of 90° C. at pressures sufficient to maintain the liquid phase. Each epoxidation run was carried out in the presence of molybdenum catalyst added as a soluble octanoate salt. The catalyst concentration, expressed as molybdenum, was 100 ppm by weight. The results obtained are shown in the following table.

| Solvent | Initial Moles Alcohol / Initial Moles HP | Moles PO Produced / Moles HP Converted |
| --- | --- | --- |
| Cyclohexane | 0.5 | 0.61 |
| Cyclohexanol | 2.2 | 0.72 |
| Cyclohexanol | 2.7 | 0.75 |

-continued

| Solvent | Initial Moles Alcohol / Initial Moles HP | Moles PO Produced / Moles HP Converted |
|---|---|---|
| Cyclohexanol | 3.9 | 0.78 |
| Tertiary butyl alcohol | 2.7 | 0.77 |
| Tertiary butyl alcohol | 3.8 | 0.79 |

From the above data it can be seen that the use of mole ratios greater than 3:1 tertiary butyl alcohol or cyclohexanol to hydroperoxide resulted in improved selectivity to propylene oxide based on hydroperoxide converted. These data clearly demonstrate that the higher amounts of tertiary and secondary alcohol are effective in improving the results achieved in the epoxidation.

What is claimed:

1. In a process for the epoxidation of propylene by catalytic reaction with cyclohexyl hydroperoxide in the presence of a $C_3$ to $C_9$ secondary or tertiary alcohol stabilizing agent, the improvement which comprises feeding 3.5:1 to 5:1 moles of alcohol stabilizer per mole of hydroperoxide to the epoxidation reaction zone.

2. The method of claim 1 wherein said alcohol stabilizing agent is a $C_3$ to $C_9$ tertiary monohydroxy alcohol.

3. The method of claim 1 wherein said alcohol stabilizer is tertiary butyl alcohol.

4. The method of claim 1 wherein said alcohol stabilizer is a $C_3$ to $C_9$ secondary monohydroxy alcohol.

5. The method of claim 1 wherein said alcohol stabilizer is cyclohexanol.

6. The process of claim 1 wherein a soluble molybdenum epoxidation catalyst is employed.

* * * * *